United States Patent
Wang

(10) Patent No.: US 7,128,862 B2
(45) Date of Patent: Oct. 31, 2006

(54) BIAXIALLY ORIENTED MULTILAYER POLYMER TUBE FOR MEDICAL DEVICES

(75) Inventor: Lixiao Wang, Long Lake, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 161 days.

(21) Appl. No.: 10/335,743

(22) Filed: Jan. 2, 2003

(65) Prior Publication Data
US 2003/0100869 A1    May 29, 2003

Related U.S. Application Data

(63) Continuation of application No. 09/898,717, filed on Jul. 3, 2001, now abandoned.

(51) Int. Cl.
B29C 47/06    (2006.01)
B29C 47/24    (2006.01)

(52) U.S. Cl. .......... 264/171.29; 264/173.16; 264/209.2; 264/209.3; 264/210.2

(58) Field of Classification Search ........ 264/108, 264/209.2, 209.8, 173.16, 209.3, 210.2, 171.26, 264/171.29; 425/381, 466, 467
See application file for complete search history.

(56) References Cited

U.S. PATENT DOCUMENTS

| | | | |
|---|---|---|---|
| 2,616,126 A | | 11/1952 | Merck et al. |
| 3,279,501 A | * | 10/1966 | Donald ...................... 138/118 |
| 3,281,897 A | * | 11/1966 | Mercer ...................... 425/380 |
| 3,404,203 A | | 10/1968 | Donald |
| 3,576,707 A | * | 4/1971 | Schrenk et al. .......... 428/36.91 |
| 3,647,612 A | * | 3/1972 | Schrenk et al. ............. 428/213 |
| 3,651,187 A | * | 3/1972 | Cessna, Jr. .................. 264/108 |
| 3,759,647 A | | 9/1973 | Schrenk et al. |
| 3,891,374 A | | 6/1975 | Ninomiya et al. |
| 3,933,960 A | * | 1/1976 | Cameron et al. ............ 264/108 |
| 3,989,785 A | * | 11/1976 | Bridge ........................ 264/564 |
| 4,039,364 A | * | 8/1977 | Rasmussen .................. 156/164 |
| 4,293,294 A | | 10/1981 | Rasmussen |
| 4,358,330 A | * | 11/1982 | Aronovici .............. 156/244.14 |
| 4,420,451 A | * | 12/1983 | Rasmussen ............ 264/171.29 |
| 4,447,239 A | | 5/1984 | Krütten |
| 4,657,024 A | | 4/1987 | Coneys |

(Continued)

FOREIGN PATENT DOCUMENTS

EP    0 662 385 A1    7/1995

(Continued)

OTHER PUBLICATIONS

Chinsirikul, W., et al., "Liquid Crystalline Polymer (LCP) Reinforced Polyethylene Blend Blown Film: Effects of Counter-Rotating Die on Fiber Orientation and Film Properties," *Polymer Engineering and Science*, vol. 36, No. 22, Nov. 1996, pp. 2708-2717.

(Continued)

*Primary Examiner*—Mark Eashoo
(74) *Attorney, Agent, or Firm*—Crompton, Seager & Tufte, LLc

(57) ABSTRACT

A tubular extruded member particularly suitable for use in medical devices such as intravascular catheters and guide wires, wherein the extruded tubular member includes multiple layers having biaxial helical orientation in different directions. A counter-rotation extrusion process may be used to orient the layers in different biaxial helical directions. The counter-rotation extrusion process provides orientation in two different circumferential directions in addition to a longitudinal direction. By combining the dual direction or biaxial helical orientation with multiple layers, different layers of the tubular member may be tailored to have the desired mechanical properties.

15 Claims, 3 Drawing Sheets

U.S. PATENT DOCUMENTS

| | | |
|---|---|---|
| 4,783,299 A | 11/1988 | Prevotat |
| 4,793,885 A * | 12/1988 | Rasmussen ................. 156/200 |
| 4,883,622 A * | 11/1989 | Dealy et al. ................. 264/108 |
| 4,885,196 A * | 12/1989 | Herrington ................. 428/36.5 |
| 4,990,143 A | 2/1991 | Sheridan |
| 5,059,375 A | 10/1991 | Lindsay |
| 5,156,785 A | 10/1992 | Zdrahala |
| 5,248,305 A | 9/1993 | Zdrahala |
| 5,456,674 A | 10/1995 | Bos et al. |
| 5,505,887 A * | 4/1996 | Zdrahala et al. ............. 264/127 |
| 5,533,985 A | 7/1996 | Wang |
| 5,622,665 A | 4/1997 | Wang |
| 5,639,409 A | 6/1997 | van Muiden |
| 5,882,741 A | 3/1999 | Rubin et al. |
| 5,947,940 A | 9/1999 | Beisel |
| 5,951,494 A | 9/1999 | Wang et al. |
| 5,961,511 A | 10/1999 | Mortier et al. |
| 5,984,657 A | 11/1999 | Bentivoglio |
| 6,045,737 A | 4/2000 | Harvey et al. |
| 6,124,007 A | 9/2000 | Wang et al. |
| 6,171,295 B1 | 1/2001 | Garabedian et al. |
| 6,242,063 B1 | 6/2001 | Ferrera et al. |
| 6,284,333 B1 | 9/2001 | Wang et al. |
| 6,436,056 B1 | 8/2002 | Wang et al. |
| 2002/0125607 A1* | 9/2002 | Herrington ............. 264/171.27 |
| 2003/0009114 A1 | 1/2003 | Chin et al. |
| 2003/0165647 A1* | 9/2003 | Kaneko et al. ............. 428/36.3 |

FOREIGN PATENT DOCUMENTS

| | | |
|---|---|---|
| JP | 63-199622 A | 8/1988 |
| JP | 2001-309533 A | 11/2001 |
| WO | WO 95/29051 A1 | 11/1995 |
| WO | WO 00/43061 A1 | 7/2000 |
| WO | WO 00/50105 A2 | 8/2000 |

OTHER PUBLICATIONS

Lusignea, R., "Flexible Multilayer Packaging with Oriented LCP Barrier Layer," *TAPPI Proceedings*, (1998) pp. 889-899.

* cited by examiner

BIAXIALLY ORIENTED MULTILAYER POLYMER TUBE FOR MEDICAL DEVICES

This application is a continuation of application Ser. No. 09/898,717 filed on Jul. 3, 2001, now abandoned.

RELATED APPLICATIONS

This application is related to co-pending patent application Ser. No. 09/898,710 filed Jul. 3, 2001, now U.S. Pat. No. 6,776,945, entitled MEDICAL DEVICE WITH EXTRUDED MEMBER HAVING HELICAL ORIENTATION, the entire disclosure of which is hereby incorporated by reference.

FIELD OF THE INVENTION

The present invention generally relates to extruded polymer tubular members for medical devices. More specifically, the present invention relates to extruded polymer tubular members for medical devices having helical orientation.

BACKGROUND OF THE INVENTION

A wide variety of medical devices utilized extruded polymeric members. For example, intravascular catheters and guide wires commonly utilize an extruded polymeric tube as a shaft component. Because intravascular catheters and guide wires must exhibit good torqueability, trackability and pushability, it is desirable that the extruded polymeric shaft component have good torque transmission, flexibility and column strength. These attributes are commonly incorporated into intravascular catheters by utilizing a composite shaft construction. Alternatively, the polymer material which forms the extruded polymeric shaft component may be oriented to enhance the mechanical characteristics thereof.

For example, U.S. Pat. No. 5,951,494 to Wang et al. discloses a variety of medical instruments, such as guide wires and catheters, formed at least in part of elongated polymer members having helical orientation. The helical orientation is established by post-processing an extruded elongate polymer member with tension, heat and twisting. Wang et al. theorize that the tension, heat and twisting process results in a polymer member that has helical orientation on the molecular level. Such molecular helical orientation enhances torque transmission of the elongate polymer member, which is important for some types of intravascular medical devices to navigate through tortuous vascular pathways.

U.S. Pat. No. 5,059,375 to Lindsay discloses an extrusion process for producing flexible kink resistant tubing having one or more spirally-reinforced sections. The extruder includes a rotatable member having an extrusion passageway for spirally extruding a thermoplastic filament into a base thermoplastic material to form a tube. The rotatable member is rotated to form the reinforcement filament in a spiral or helical pattern in the wall of the tubing.

U.S. Pat. No. 5,639,409 to Van Muiden discloses an extrusion process for manufacturing a tube-like extrusion profile by conveying a number of divided streams of material of at least two different compositions through a rotating molding nozzle. The streams of material flow together in the rotating molding nozzle to form at least two helically shaped bands of material. After allowing the combined streams of material to cool off, an extrusion profile comprising a plurality of bands of material extending in a helical pattern is formed.

U.S. Pat. No. 5,248,305 to Zdrahala discloses a method of manufacturing extruded catheters and other flexible plastic tubing with improved rotational and/or longitudinal stiffness. The tubing comprises a polymer material including liquid crystal polymer (LCP) fibrils extruded through a tube extrusion die while rotating the inner and outer die walls to provide circumferential shear to the extruded tube. Rotation of the inner and outer die walls orients the LCP in a helical manner to provide improved properties, including greater rotational stiffness.

Although each of these prior art methods provide some degree of orientation which enhances the mechanical characteristics of extruded polymeric members, there is an ongoing need to further enhance the mechanical characteristics of medical devices such as intravascular catheters and guide wires to improve performance thereof.

SUMMARY OF THE INVENTION

The present invention provides a tubular extruded member particularly suitable for use in medical devices such as intravascular catheters and guide wires, wherein the extruded tubular member includes multiple layers having biaxial helical orientation in different directions. A counter-rotation extrusion process may be used to orient the layers in different helical directions. The counter-rotation extrusion process provides orientation in two different circumferential directions in addition to a longitudinal direction. By combining the dual direction helical orientation with multiple layers, different layers of the tubular member may be tailored to have the desired mechanical properties. Thus, for example, to increase torque transmission of an intravascular guide wire, the outer layer may be formed of a relatively rigid material. To increase column strength and/or kink resistance of an intravascular catheter, the inner layer may be formed of a relatively soft and flexible material. To increase burst strength of an intravascular balloon, the inner layer may incorporate a relatively hard and thin material. To increase puncture resistance of an intravascular balloon, the outer layer may be formed of a relatively soft and durable material. In each instance, the multi-layer tube incorporates biaxial helical orientation in different directions to enhance the mechanical properties thereof.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 2:
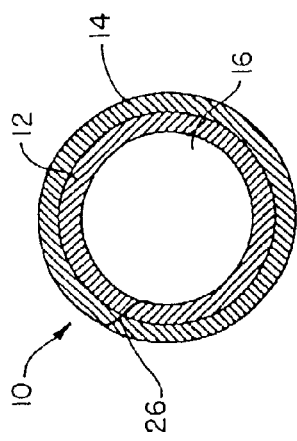
FIG. 2 is a cross-sectional view taken along line 2—2 in FIG. 1.
Figure 1:
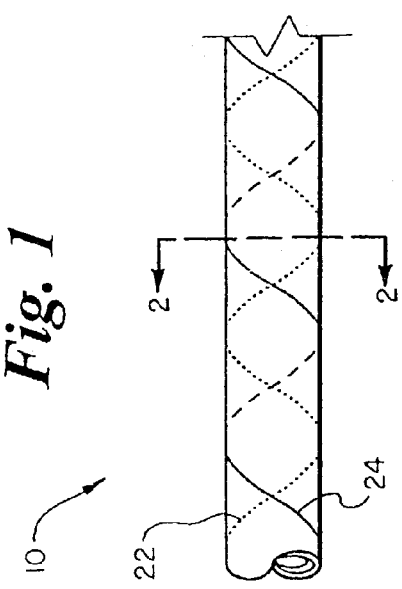
FIG. 1 is a plan view of a multi-layered extruded tube in accordance with an embodiment of the present invention.

Refer now to FIG. 1 which illustrates a tubular polymer extruded member 10 in accordance with the present invention. Extruded tubular polymer member 10 includes a plurality of coaxial tubular layers 12/14 and a lumen 16 as best seen in FIG. 2, which is a cross-sectional view taken along line 2—2 in FIG. 1. For purposes of illustration only, the tubular member 10 is shown to include two layers, namely an inner layer 12 and an outer layer 14. It is to be understood, however, that the tubular member 10 may incorporate virtually any number of concentric tubular layers, depending on the desired characteristics of the tubular member 10.

The tubular member 10 has orientation in two different circumferential directions as indicated by reference lines 22 and 24. Reference line 22 illustrates the helical orientation of the inner tubular layer 12 and reference line 24 illustrates the helical orientation of outer layer 14. Reference line 26 shown in FIG. 2 illustrates the different rotational directions of the biaxial helical orientation. In this particular example, reference line 26 illustrates clockwise rotational orientation in the outer layer 14 and counter-clockwise rotational orientation in the inner layer 12. It is to be understood that the rotational orientation may be reversed. In particular, the outer layer 14 may have counter-clockwise rotational orientation and the inner layer 12 may have clockwise rotational orientation.

By combining the dual direction or biaxial helical orientation with multiple layers 12/14, different layers of the tubular member 10 may be tailored to have the desired mechanical properties. For example, the outer layer 14 may include a helically oriented relatively rigid material to increase torsional rigidity. Alternatively, the inner layer 12 may include a helically oriented relatively rigid material to increase hoop strength (i.e., burst strength). As a further alternative, the inner layer 12 may include a helically oriented relatively flexible material to increase kink resistance. As yet a further alternative, the outer layer 14 may include a helically oriented relatively durable material to increase puncture resistance. These and other examples of tubular member 10 are particularly useful when incorporated into a medical device such as catheter 30 described with reference to FIG. 3.

Figure 3:
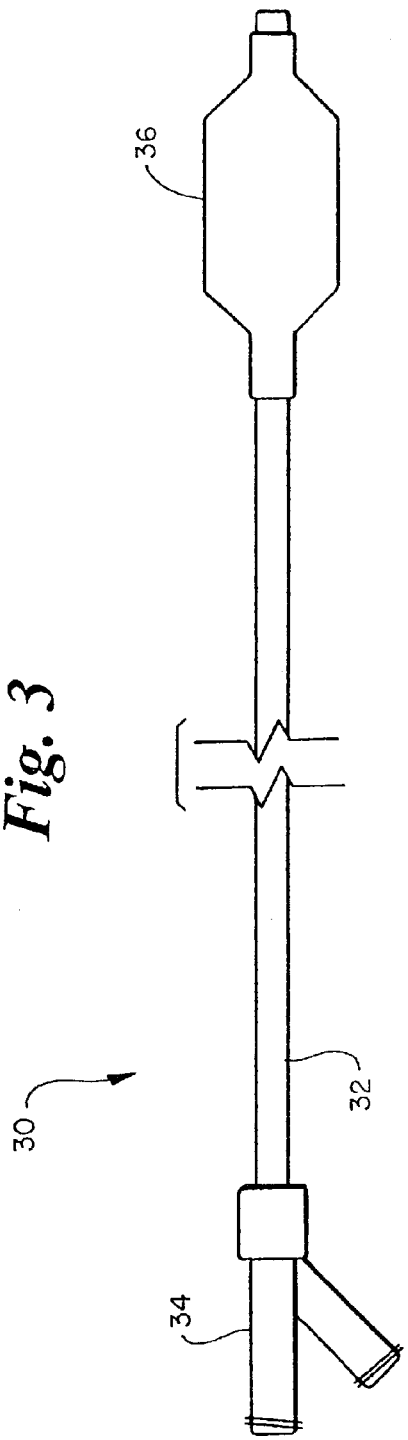
FIG. 3 is a plan view of an intravascular balloon catheter incorporating the tubular member illustrated in FIG. 1.

FIG. 3 illustrates an intravascular balloon catheter 30, which is substantially conventional with the exception of incorporating one or more of the several embodiments of the tubular member 10 described with reference to FIG. 1. The intravascular balloon catheter 30 includes an elongate shaft 32 having a proximal end and a distal end. A conventional manifold 34 is connected to the proximal end of the elongate shaft 32. An inflatable balloon 36 is connected to the distal end of the elongate shaft 32. The elongate shaft 32 may be formed at least in part of the multi-layer tube 10 described with reference to FIGS. 1 and 2. In addition, the balloon 36 may be formed at least in part from a blow-molded multi-layer tube 10.

As mentioned previously, providing a multi-layer tube 10 allows each of the individual layers 12/14 to be tailored with the desired features. For example, the inner layer 12 may be formed of a relatively hard and rigid polymeric material. Concentrating the relatively hard and rigid polymeric material in the inner layer 12 increases hoop strength (i.e., burst strength) and improves kink resistance of the tubular member 10. Providing a catheter 30 having a shaft 32 and a balloon 36 that is able to withstand high inflation pressures is advantageous for certain clinical applications requiring high inflation pressure. Providing a catheter 30 having a shaft 32 that is kink resistant is advantageous because damage due to handling and/or navigation through tortuous vasculature is mitigated.

Alternatively, the inner layer 12 may be formed of a relatively soft and flexible polymeric material. Concentrating the relatively soft and flexible polymeric material in the inner layer 12 improves kink resistance of the tubular member 10 if the outer layer 14 is formed of a material susceptible to kinking. As mentioned above, providing a catheter 30 having a shaft 32 that is kink resistant is advantageous because damage due to handling and/or navigation through tortuous vasculature is mitigated.

The outer layer 14 may comprise a relatively hard and rigid polymeric material. Concentrating the relatively hard and rigid polymeric material in the outer layer 14 increases rotational stiffness and column strength of the tubular member 10. Providing an intravascular guide wire having a shaft with increased rotational stiffness is advantageous in clinical applications requiring 1:1 torque response for precise steering, particularly in tortuous vasculature. In addition, providing an intravascular guide wire and/or catheter 30 having a shaft 32 with increased column strength is advantageous in clinical applications requiring substantial longitudinal force transmission over long distances as is usually required to cross tight vascular restrictions.

Alternatively, the outer layer 14 may be formed of a relatively soft and flexible polymeric material. Concentrating a relatively soft and flexible polymeric material in the outer layer 14 improves the durability of the tubular member 10. Providing a catheter 30 having a balloon 36 with increased durability mitigates the likelihood of balloon burst due to puncture from a calcified vascular deposit or from a stent.

When utilized to form a portion of the elongate shaft 32, the multi-layer tube 10 may have a wall thickness ranging from approximately 0.002 inches to 0.010 inches, and a length ranging from 10 cm to 150 cm. When utilized to form the balloon 36, the multi-layer tube 10 may have a wall thickness (post blow-molding) ranging from 0.0005 inches to 0.002 inches, and a length ranging from 1 cm to 10 cm. These dimensions are provided by way of example, not limitation.

The relative thickness and material composition of each layer 12/14 may be modified to balance the respective properties of the elongate shaft 32 or balloon 36. For example, the thickness of the inner and outer layers of 12/14 may be modified and/or the materials selected for the inner and outer layers 12/14 may be modified.

Examples of suitable rigid polymers include polyurethane (isoplastic), aromatic polyamide, polyamide, PET, PEN, LCP, polycarbonate, aromatic polyester, etc. Examples of suitable soft and flexible polymers include polyurethane elastamers, polyether block amides (PEBA), Pellethane, Hytrel, Amitel, Estane, Pebax, Grilamid, Vestamid, Riteflex, etc.

A specific example of a hard-soft multiple-layer combination is one layer formed of a polyamide (e.g., nylon or PEBA) and another layer formed of polyethylene with a tie-layer of polyethylene copolymer disposed therebetween. Another specific example of a hard-soft multiple-layer combination is one layer formed of aromatic nylon and the other layer formed of nylon 12.

The inner and/or outer layers 12/14 may also comprise a reinforced polymer structure such as a polymer layer including continuous liquid crystal polymer fibers (LCP) dispersed in a non-LCP thermal plastic polymer matrix. The LCP content of the LCP containing layer may be greater than 0.1% by weight and less than 90% by weight. In addition, for enhanced performance, the LCP containing layer may comprise 0.05% to 50% by weight of the combined layers.

Figure 4:
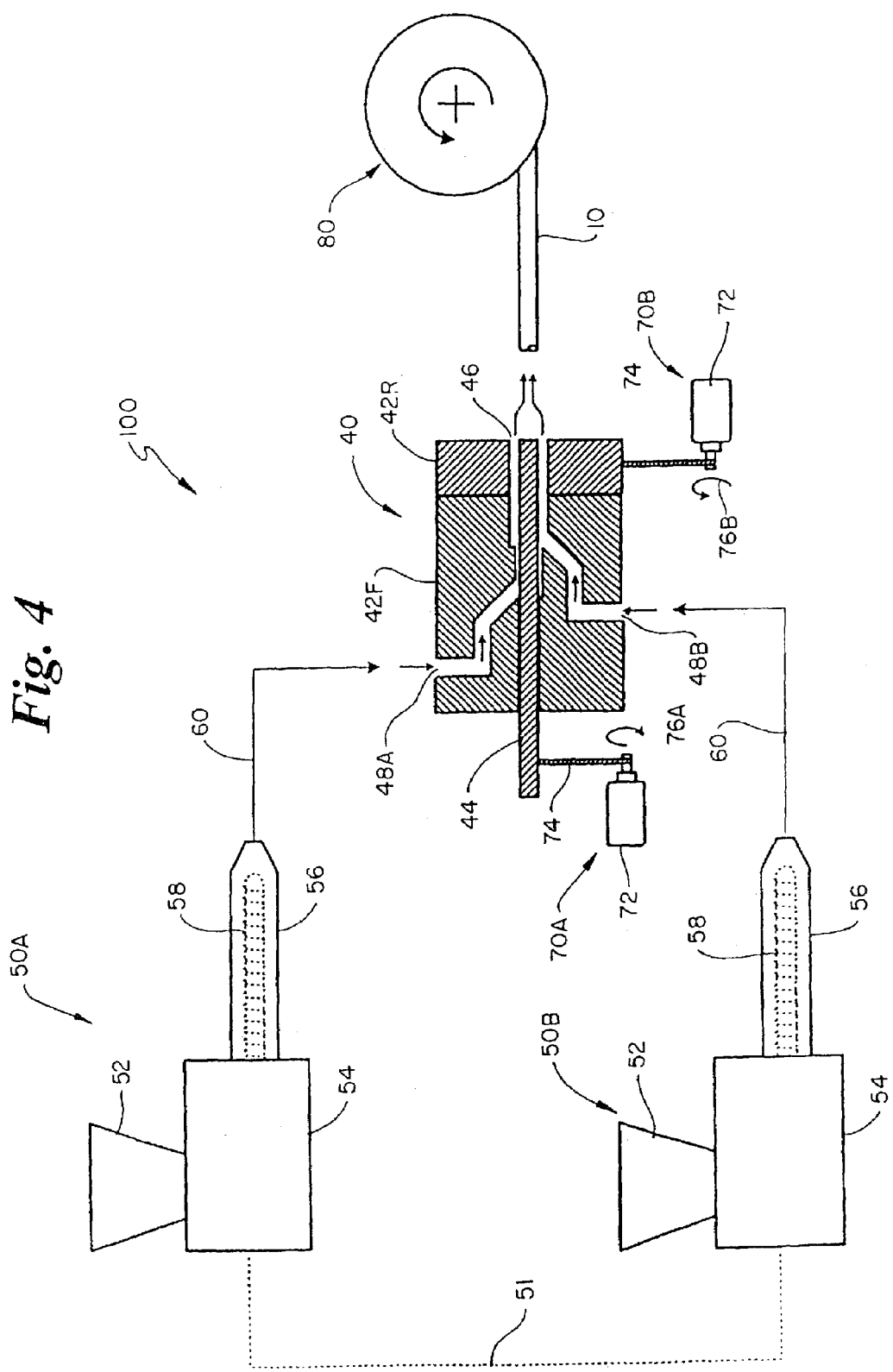
FIG. 4 is a schematic illustration of an extrusion process for manufacturing the tubular member illustrated in FIG. 1.

Refer now to FIG. 4 which illustrates an extrusion system 100 for manufacturing the multi-layer tubular member 10 discussed with reference to FIGS. 1 and 2. Extrusion system 100 includes one or more extruders 50A/50B coupled to an extrusion head 40 as schematically illustrated by extrusion lines 60. Each extruder 50A/50B includes a hopper 52, a heated barrel 56, an extrusion screw 58, and a control system 54. The control system 54 of each extruder 50A/50B is operably coupled as indicated by dashed line 51 to facilitate co-extrusion.

Extrusion head 40 includes an outer die portion 42 having a fixed portion 42F and a rotatable portion 42R. Extrusion head 40 further includes a rotatable pin 44 rotatably disposed in the outer die portions 42F and 42R. Molten polymer enters the extrusion head 40 at inlets 48A and 48B. The molten polymer entering inlet 48A forms the inner layer 12 and the molten polymer entering inlet 48B forms the outer layer 14 of the multi-layer extrusion 10. The molten polymer flows through the extrusion passages as indicated by the small arrows. The molten polymer exits the extrusion head 40 through outlet 46. Upon exiting the extrusion head 40 through outlet 46, the molten polymer begins to solidify to form the multi-layer tube 10 which may be subsequently cut to length or taken up by spool 80.

The rotatable pin 44 is coupled to a rotational drive 70A which rotates in the direction indicated by arrow 76A. The rotational drive 70A may comprise, for example, a motor 72 coupled to the rotational pin 44 by a chain or belt 74. Similarly, the rotational outer die 42R is connected to rotational drive 70B which rotates in the direction indicated by arrow 76B. Note that the direction of rotation of drive 70A is different than the rotational direction of drive 70B, thereby rotating the pin 44 in a different direction than the outer die 42R.

As the molten polymer exits the extrusion head 40 through outlet 46, the rotatable outer die imparts helical orientation to the outer layer 14 of the tubular member 10. In addition, as the molten polymer exits the outlet 46 of the extrusion head 40, the rotating pin 44 imparts helical orientation to the inner layer 12 of the tubular member 10. Because the pin 44 is rotated in the opposite direction of rotatable outer die 42R, the helical orientation imparted to the outer layer 14 is in the opposite direction of the helical orientation imparted to the inner layer 12. Although not shown, an air passage may extend through the pin 44, which may be used to pump air into the tubular member 10 as it solidifies to help maintain the lumen 16 therein. As the molten polymer begins to solidify after exiting through outlet 46, the biaxial helical orientation imparted to the inner and outer layers 12/14 is locked into the tubular member 10.

Figure 5:
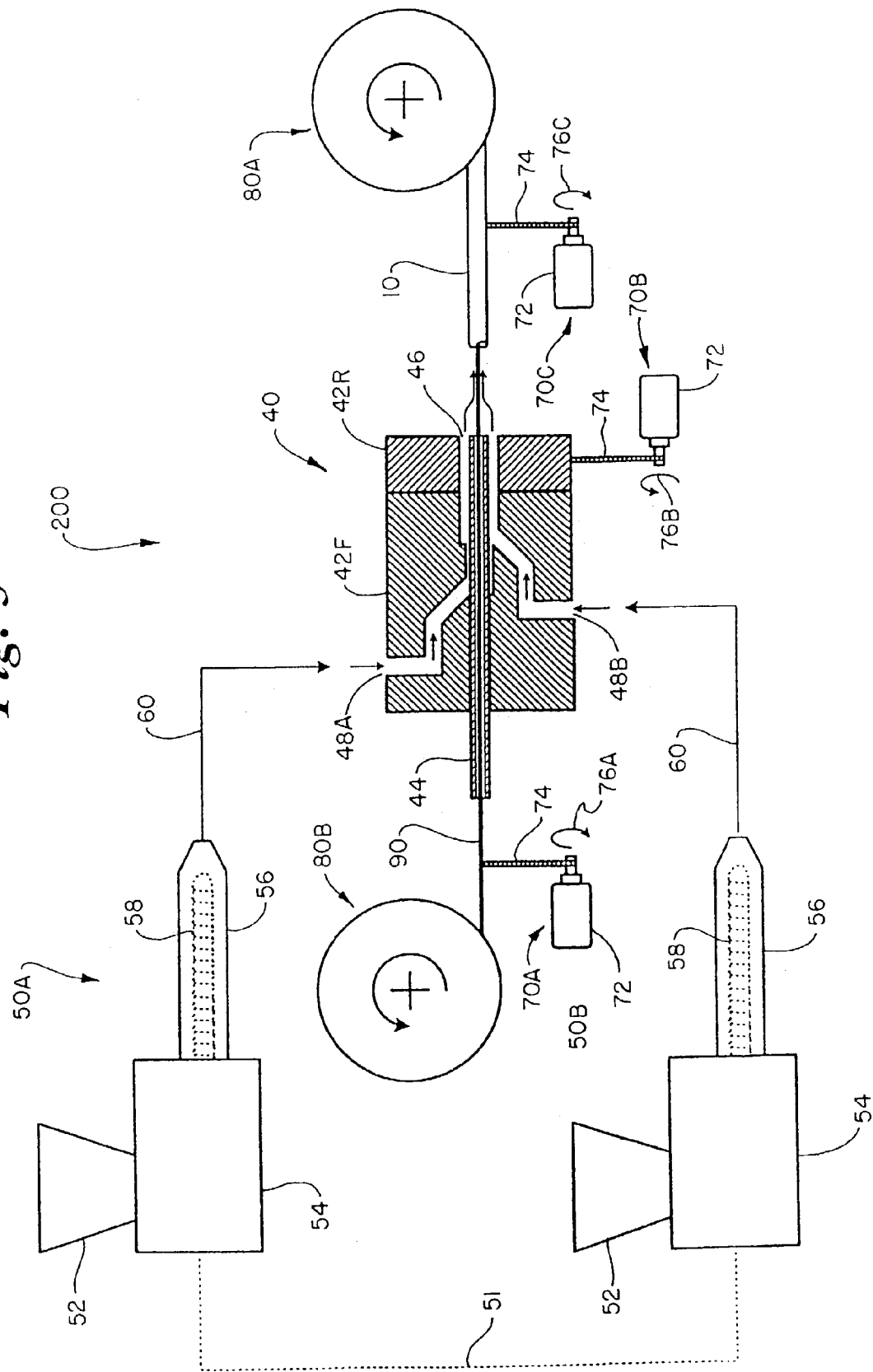
FIG. 5 is a schematic illustration of an alternative manufacturing process for manufacturing the tubular member illustrated in FIG. 1.

Refer now to FIG. 5 which illustrates an alternative extrusion system 200 for manufacturing the multi-layer tubular member 10. Except as described herein, the extrusion system 200 is similar to the extrusion systems described in co-pending patent application Ser. No. 09/898,710, filed on even date herewith, entitled MEDICAL DEVICE WITH EXTRUDED MEMBER HAVING HELICAL ORIENTATION, the entire disclosure of which is hereby incorporated by reference.

Extrusion system 200 includes two or more extruders 50A/50B coupled to extrusion head 40 substantially as described previously. However, in this embodiment, the pin 44 remains stationary and is hollow to serve as a guide for mandrel 90. Molten polymer enters the extrusion head 40 at inlets 48A/48B and flows through the extrusion passages as indicated by the small arrows. The molten polymer exits the extrusion head 40 through outlet 46. Upon exiting the extrusion head 40 through outlet 46, the molten polymer begins to solidify thereby creating a semi-molten polymer state. In a semi-molten state, the polymer typically has a temperature below the melting point but at or above the glass transition point.

In this semi-molten state, the multi-layer tubular member 10 is rotated by rotational drive 70C in a direction indicated by arrow 76C. The support mandrel 90 is also rotated by a rotational drive 70A in a direction indicated by arrow 76A. The support mandrel 90 and the multi-layered tubular member 10 are rotated in the same direction, while the rotational outer die 42R is rotated in the opposite direction by rotational drive 70B as indicated by arrow 76B.

By rotating the multi-layer tubular member 10 in the semi-molten state, a molecular helical orientation is imparted to both the inner layer 12 and the outer layer 14. In particular, in the semi-molten state, the crystalline regions of the polymer are helically oriented by rotation and subsequently allowed to cool thereby locking in the biaxial helical orientation on the molecular level. Helical orientation is also imparted to the outer tubular layer 14 in the opposite direction by virtue of the rotating outer die 42R. The multi-layer tubular member 10 may be cut into discrete lengths immediately after extrusion or spooled onto take-up spool 80A. If the multi-layer tubular member 10 is taken-up by spool 80A, the multi-layer tubular member 10 and the spool 80A may be rotated simultaneously. Similarly, if the support mandrel 90 is provided on a spool 80B, the spool 80B and the support mandrel 90 may be rotated simultaneously.

A further alternative extrusion system for manufacturing the multi-layer tubular member 10 is partially disclosed in U.S. Pat. No. 5,622,665 to Wang, the entire disclosure of which is hereby incorporated by reference. Wang '665 discloses a method for making differential stiffness tubing for medical products, such as catheters. The method produces a tubing that has a stiff section and a flexible section joined by a relatively short transition section in which the materials of the stiff and flexible sections are wedged into each other in a smooth gradual manner to produce an inseparable bond between the materials without abrupt joints. The method also employs a resin modulating system that minimizes the length of the transition section by minimizing the volumes in all flow channels of the co-extrusion head used to produce the tubing.

Wang '665 further discloses a system for co-extruding differential stiffness tubing. The system includes a co-extrusion head into which extruders feed the different resins, such as a soft resin and a stiff resin, that will be used to form the finished tubing. A modulating device regulates the flow of the resins from each of the extruders into the co-extrusion head, while another modulator may be used to bleed resin "A" from the head to relieve residual pressure. To produce tubing with differential stiffness, the modulators are actuated periodically and in synchronized fashion to abruptly stop or change the resin flow to the head. Because of the design of co-extrusion head, the interface between the stiff resin and soft resin is naturally sheared and elongated when flowing through the flow channels of the head. Thus, these abrupt changes or stoppages by the modulators result in a very gradual change of stiff layer thickness in the tubing, creating the gradual stiffness change of the tubing. After discharge from the head, the tubing is cooled by passage through a water tank to form the tubing.

The system disclosed by Wang '665 may be modified for purposes of the present invention. In particular, as with the extrusion system discussed with reference to FIG. 4 of the present application, a rotational drive may be coupled to the pin in the co-extrusion head of Wang '665, and a rotational drive may be coupled to the die of Wang '665, with the necessary modifications made to the co-extrusion head to permit such rotation. The rotational drives may comprise, for example, a motor coupled to the pin and die by a chain or belt. The direction of rotation of the pin drive is different than the rotational direction of the die drive, thereby rotating the pin in a different direction than the die.

As the molten polymer exits the modified co-extrusion head of Wang '665, the rotatable die imparts helical orientation to the outer layer 14 of the tubular member 10 and the rotatable pin imparts helical orientation to the inner layer 12 in the opposite direction. Although not shown, an air passage may extend through the pin 44, which may be used to pump air into the tubular member 10 as it solidifies to help maintain the lumen 16 therein. As the molten polymer begins to solidify after exiting through the modified extrusion head of Wang '665, the biaxial helical orientation imparted to the inner and outer layers 12/14 is locked into the tubular member 10.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of forming a biaxially oriented multi-layer tube of a medical device, comprising steps of:
    providing a first polymer and a second polymer to an extruder,
    co-extruding an inner layer comprising the first polymer and an outer layer comprising the second polymer through a counter-rotating die comprising an inner die rotating in a first direction and an outer die rotating in a second direction opposite that of the first direction, thereby forming a multi-layer tube;
    rotating the multi-layer tube in a direction equal to the first direction while the multi-layer tube is in a semi-molten state; and
    cooling the semi-molten multi-layer tube to form a biaxially oriented multi-layer tube;
    wherein the inner layer of the resulting biaxially oriented multi-layer tube has a biaxial helical orientation on a molecular scale and the outer layer of the resulting biaxially oriented multi-layer tube has an opposing biaxial helical orientation on a molecular scale.

2. The method of claim 1, wherein the semi-molten state is defined by the polymer forming the inner layer and the polymer forming the outer layer being at a temperature that is intermediate a glass transition temperature of each polymer and a melting temperature of each polymer.

3. The method of claim 1, wherein the step of providing a first polymer and a second polymer comprises providing a relatively flexible polymeric material for one of the first and second polymers and a relatively rigid polymeric material for the other of the first and second polymers.

4. The method of claim 1, wherein the step of providing a first polymer and a second polymer comprises providing continuous liquid crystal polymer fibers dispersed in a non-liquid crystal polymer matrix.

5. The method of claim 1, wherein the first polymer is provided through a first inlet and the second polymer is provided through a second inlet.

6. The method of claim 1, wherein the outer layer and the inner layer are concentric tubular layers of the multi-layer tube.

7. A method of forming a biaxially oriented multi-layer tubular medical device, comprising the steps of:
    providing an extrusion system comprising a counter-rotating extrusion die including a rotatable inner die and a rotatable outer die;
    co-extruding an inner layer comprising a first polymer and an outer layer comprising a second polymer through the extrusion die, wherein the inner die is rotated in a first direction and the outer die is rotated in a second direction opposite that of the first direction, thereby forming a multi-layer tube, wherein the inner layer and the outer layer are concentric tubular layers;
    rotating the multi-layer tube in a direction equal to the first direction while the multi-layer tube is in a semi-molten state; and
    cooling the semi-molten multi-layer tube to form a biaxially oriented multi-layer tube;
    wherein the inner layer of the resulting biaxially oriented multi-layer tube has a biaxial helical orientation on a molecular scale and the outer layer of the resulting biaxially oriented multi-layer tube has an opposing biaxial helical orientation on a molecular scale.

8. The method of claim 7, wherein the semi-molten state is defined by the polymer forming the inner layer and the polymer forming the outer layer being at a temperature that is intermediate a glass transition temperature of each polymer and a melting temperature of each polymer.

9. The method of claim 7, wherein one of the first and second polymer comprises a relatively flexible polymeric material and the other of the first and second polymer comprises a relatively rigid polymeric material.

10. The method of claim 7, wherein at least one of the first and second polymer comprises liquid crystal polymer fibers dispersed in a non-liquid crystal polymer matrix.

11. A method of forming a biaxially oriented multi-layer tubular medical device, comprising the steps of:
    providing an extrusion system comprising a counter-rotating extrusion die including a rotatable inner die and a rotatable outer die;
    providing a first polymer to the extrusion die through a first inlet;
    providing a second polymer to the extrusion die through a second inlet;
    co-extruding an inner layer comprising the first polymer and an outer layer comprising the second polymer through the extrusion die, wherein the inner die is rotated in a first direction and the outer die is rotated in a second direction opposite that of the first direction, thereby forming a multi-layer tube;
    rotating the multi-layer tube in a direction equal to the first direction while the multi-layer tube is in a semi-molten state; and
    cooling the semi-molten multi-layer tube to form a biaxially oriented multi-layer tube;
    wherein the inner layer of the resulting biaxially oriented multi-layer tube has a biaxial helical orientation on a molecular scale and the outer layer of the resulting biaxially oriented multi-layer tube has an opposing biaxial helical orientation on a molecular scale.

12. The method of claim 11, wherein the semi-molten state is defined by the polymer forming the inner layer and the polymer forming the outer layer being at a temperature that is intermediate a glass transition temperature of each polymer and a melting temperature of each polymer.

13. The method of claim 11, wherein the outer layer and the inner layer are concentric tubular layers.

14. The method of claim 11, wherein at least one of the first and second polymer comprises liquid crystal polymer fibers dispersed in a non-liquid crystal polymer matrix.

15. The method of claim 11, wherein one of the first and second polymer comprises a relatively flexible polymeric material and the other of the first and second polymer comprises a relatively rigid polymeric material.

* * * * *

UNITED STATES PATENT AND TRADEMARK OFFICE
CERTIFICATE OF CORRECTION

PATENT NO. : 7,128,862 B2
APPLICATION NO. : 10/335743
DATED : October 31, 2006
INVENTOR(S) : Lixiao Wang It is certified that error appears in the above-identified patent and that said Letters Patent is hereby corrected as shown below:

Column 4
Line 54, delete "Amitel" and insert therefor -- Arnitel --.

Signed and Sealed this

Twentieth Day of February, 2007

JON W. DUDAS
*Director of the United States Patent and Trademark Office*